(12) United States Patent
Moore

(10) Patent No.: US 7,712,575 B1
(45) Date of Patent: May 11, 2010

(54) SPIRAL CUT STETHOSCOPE WRAP

(76) Inventor: Willie L Moore, 8631 Richard Ct., University City, MO (US) 63132

( * ) Notice: Subject to any disclaimer, the term of this patent is extended or adjusted under 35 U.S.C. 154(b) by 12 days.

(21) Appl. No.: 11/847,076

(22) Filed: Aug. 29, 2007

(51) Int. Cl.
- *A61B 7/02* (2006.01)
- *A61B 5/021* (2006.01)
- *A61B 5/024* (2006.01)
- *A61B 7/00* (2006.01)
- *A61B 5/02* (2006.01)
- *A61B 5/022* (2006.01)

(52) U.S. Cl. ...................................... 181/131; 600/528
(58) Field of Classification Search ................. 181/131; 600/528; 381/67; D24/134
See application file for complete search history.

(56) References Cited

U.S. PATENT DOCUMENTS

| | | | | |
|---|---|---|---|---|
| 2,713,383 A | * | 7/1955 | Kennedy | 156/86 |
| 4,121,686 A | * | 10/1978 | Keller, Jr. | 181/233 |
| 4,373,718 A | * | 2/1983 | Schmidt | 473/538 |
| 4,431,469 A | * | 2/1984 | Falcomato | 156/86 |
| 4,806,400 A | * | 2/1989 | Sancaktar | 428/35.9 |
| 4,860,851 A | * | 8/1989 | Krevor et al. | 181/207 |
| 5,108,368 A | * | 4/1992 | Hammerslag et al. | 604/528 |
| 5,378,234 A | * | 1/1995 | Hammerslag et al. | 604/95.04 |
| 5,466,898 A | * | 11/1995 | Gilbert et al. | 181/131 |
| 5,539,162 A | * | 7/1996 | Tuttle | 181/131 |
| D376,043 S | * | 12/1996 | Rix | D3/203.1 |
| 5,592,946 A | * | 1/1997 | Eddy | 600/528 |
| 5,623,131 A | * | 4/1997 | Earnest | 181/131 |
| 6,006,856 A | * | 12/1999 | Skubal et al. | 181/131 |
| 6,165,035 A | * | 12/2000 | Avner | 446/72 |
| 6,186,957 B1 | * | 2/2001 | Milam | 600/528 |
| D455,254 S | * | 4/2002 | Sanchez-Thomas | D3/203.1 |
| 6,575,917 B2 | * | 6/2003 | Giroux et al. | 600/528 |
| 6,629,547 B1 | * | 10/2003 | Yamaguchi et al. | 138/129 |
| 6,773,774 B1 | * | 8/2004 | Crook et al. | 428/34.7 |
| 2002/0170771 A1 | * | 11/2002 | Milam et al. | 181/131 |
| 2003/0221903 A1 | * | 12/2003 | Roby et al. | 181/131 |
| 2004/0256172 A1 | * | 12/2004 | Darling | 181/131 |
| 2007/0193822 A1 | * | 8/2007 | Statner et al. | 181/131 |

FOREIGN PATENT DOCUMENTS

DE          3909011 A1 * 10/1989

* cited by examiner

*Primary Examiner*—Edgardo San Martin
(74) *Attorney, Agent, or Firm*—Polster, Lieder, Woodruff & Lucchesi, LC

(57) ABSTRACT

A stethoscope protective wrap for a stethoscope including a pair of ear inserts attached to a pair of arms, a sound tube and a stethoscope head, the wrap including a protective wrap installed over the sound tube of the stethoscope, the protect wrap comprising a spiral cut material. A method of assembling the stethoscope is also provided.

5 Claims, 2 Drawing Sheets

SPIRAL CUT STETHOSCOPE WRAP

FIELD OF THE INVENTION

The invention relates to stethoscopes. More specifically, the invention relates to a device for the protection of stethoscopes.

BACKGROUND OF THE INVENTION

This invention relates to preserving the life of the stethoscope due to body oils. Prior to this idea, the only alternative was to place a cloth cover over the stethoscope if it was carried around the neck. The disadvantage of the cloth cover was the exposure to health-related germs and the soiling due to the oils excreted around the neck which could lead to contamination of other patients.

BRIEF DESCRIPTION OF THE DRAWINGS

FIG. 3 is a view of a stethoscope protective wrap being applied to a stethoscope according to an embodiment of the present invention.

SUMMARY OF THE INVENTION

Figure 1:
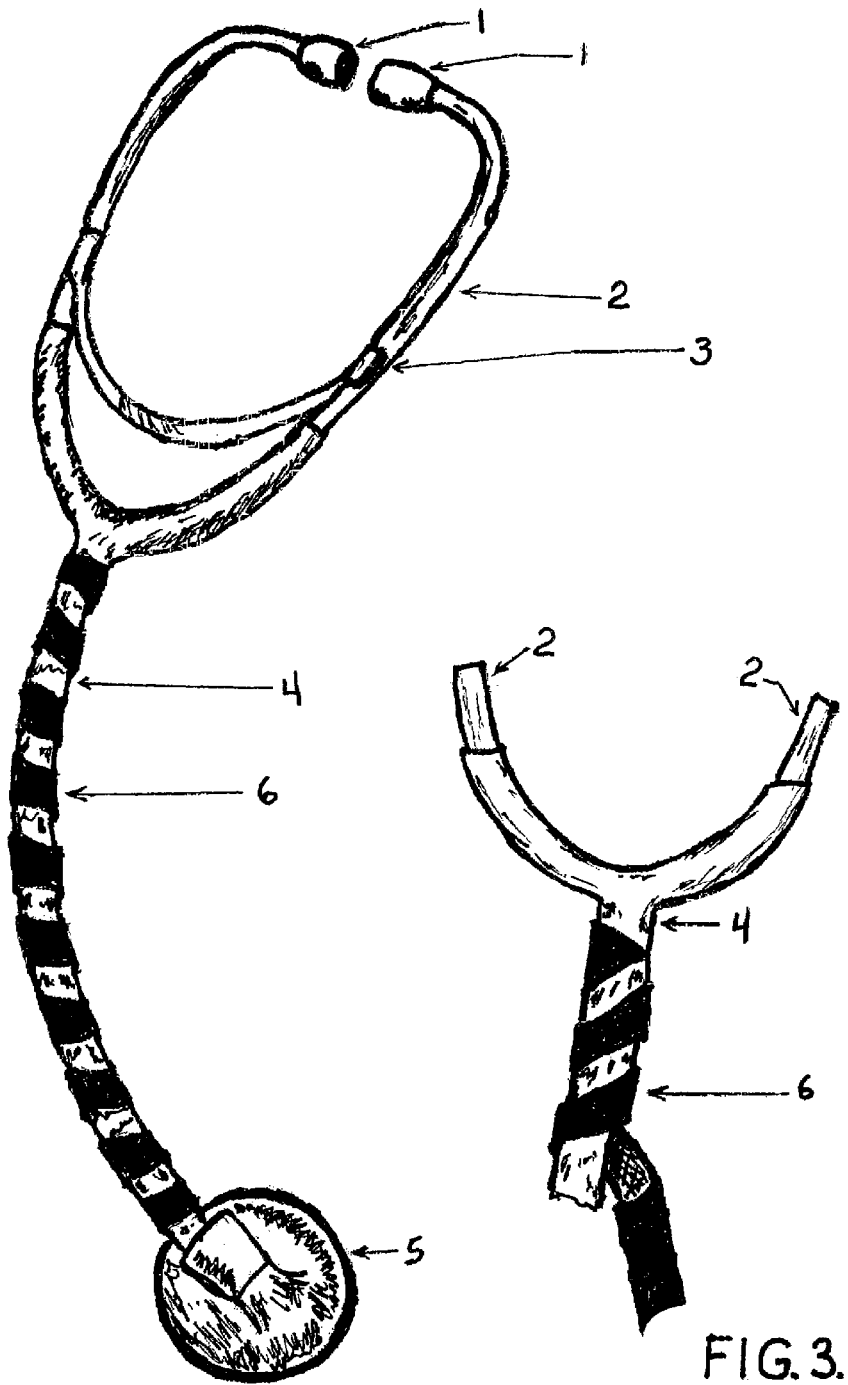
FIG. 1 is a view of a stethoscope with a protective wrap according to an embodiment of the present invention.

A stethoscope protective wrap for a stethoscope including a pair of ear inserts attached to a pair of arms, a sound tube and a stethoscope head, the wrap including a protective wrap installed over the sound tube of the stethoscope, the protect wrap comprising a spiral cut material. A method of assembling the stethoscope is also provided.

DESCRIPTION OF THE PREFERRED EMBODIMENT

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

This invention is designed to not only protect the stethoscope from body oils, but is also aimed to allow easy removal for cleaning. The various colors will also make each stethoscope unique. Since the medical field has chosen to allow various colored uniforms, this invention can enhance the fashionable attire of the medical profession.

Figure 2:
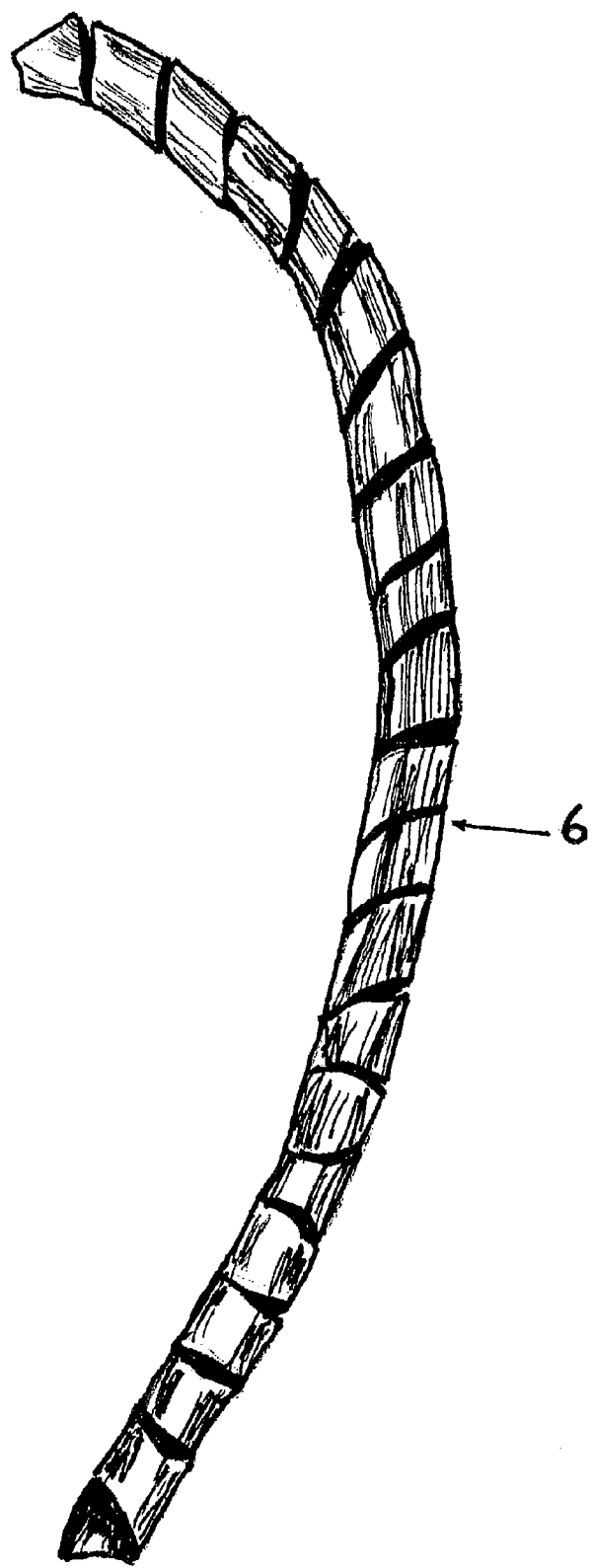
FIG. 2 is a view of a stethoscope protective wrap according to an embodiment of the present invention.

Referring to FIG. 1, there is shown a stethoscope cover 6 in accordance with an embodiment of the present invention. The stethoscope comprises a pair of ear inserts 1, stethoscope arms 2, a spring member 3, a sound tube 4 and a stethoscope head 5. Referring to FIG. 2, the stethoscope cover 6 comprises a length of spiral cut tubing. Preferably, the stethoscope cover 6 is made from polyethylene. Referring to FIG. 3, the stethoscope cover 6 is applied to an existing and fully constructed stethoscope by continuously wrapping the sound tube 4 of the stethoscope with the spiral cut tubing of the stethoscope cover 6. When the stethoscope cover 6 becomes soiled or needs to be disinfected, it can easily be removed from the stethoscope. The stethoscope cover 6 thereby protects the stethoscope from soil and wear, and particularly from body oils when the stethoscope is worn by a person by placing the sound tube around the back of one's neck.

The stethoscope is constructed by first providing a fully assembled stethoscope having a sound tube and then applying a protective wrap comprising a spiral cut material to the stethoscope sound tube by curling the spiral wrap around the sound tube.

The above examples show that the invention, as defined by the claims, has far ranging application and should not be limited merely to the embodiments shown and described in detail. Instead the invention should be limited only to the explicit words of the claims, and the claims should not be arbitrarily limited to embodiments shown in the specification. The scope of protection is only limited by the scope of the accompanying claims, and the Examiner should examine the claims on that basis.

I claim:

1. A stethoscope comprising:
a pair of ear inserts attached to a pair of arms;
a sound tube and a stethoscope head;
a protective wrap installed over the sound tube of the stethoscope, the protective wrap comprising a length of tubing having a spiral cut therein from a first to second end of the tube and rotating around its circumference such that tubing may be applied to the sound tube along the length of the sound tube by passing the sound tube through the spiral cut of the tubing and the tubing may be removed and replaced from the sound tube by passing the sound tube back through the spiral cut such that the protective wrap may be easily removed without disassembly of the stethoscope, the tubing not being dispensed from a roll, the protective wrap not being adhered to the sound tube but rather loosely placed over the sound tube and maintained in place by the resiliency of the spiral cut tube, the spiral cut tubing applied along substantially the entire length of the sound tube.

2. The stethoscope of claim 1 wherein the protective wrap is made from polyethylene.

3. A method of constructing a stethoscope comprising a stethoscope protective wrap comprising the steps of:
providing a fully assembled stethoscope having a sound tube;
applying a protective wrap comprising a spiral cut material to the stethoscope sound tube by curling the spiral wrap around the sound tube, the protective wrap consisting of:
a length of tubing having a spiral cut therein from a first to second end of the tube and rotating around its circumference such that tubing may be applied to the sound tube along the length of the sound tube by passing the sound tube through the spiral cut of the tubing and the tubing may be removed and replaced from the sound tube by passing the sound tube back through the spiral cut such that the protective wrap may be easily removed without disassembly of the stethoscope, the tubing not being dispensed from a roll, the protective wrap not being adhered to the sound tube but rather loosely placed over the sound tube and maintained in place by the resiliency of the spiral cut tube, the spiral cut tubing applied along substantially the entire length of the sound tube.

4. The stethoscope of claim 3 wherein the protective wrap is made from polyethylene.

5. A stethoscope consisting of:
a pair of ear inserts attached to a pair of arms;
a sound tube and a stethoscope head;
a protective wrap installed over the sound tube of the stethoscope, the protective wrap comprising a length of tubing having a spiral cut therein from a first to second end of the tube and rotating around its circumference such that tubing may be applied to the sound tube along the length of the sound tube by passing the sound tube through the spiral cut of the tubing and the tubing may be removed and replaced from the sound tube by passing the sound tube back through the spiral cut such that the protective wrap may be easily removed without disassembly of the stethoscope, the tubing not being dispensed from a roll, the protective wrap not being adhered to the sound tube but rather loosely placed over the sound tube and maintained in place by the resiliency of the spiral cut tube, the spiral cut tubing applied along substantially the entire length of the sound tube.

* * * * *